United States Patent
Oshika et al.

(10) Patent No.: US 8,524,205 B2
(45) Date of Patent: Sep. 3, 2013

(54) HAIR COSMETIC COMPOSITION

(75) Inventors: Masato Oshika, Tokyo (JP); Yoshihiko Watanabe, Wakayama (JP); Masayoshi Ehara, Darmstadt (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/144,647

(22) PCT Filed: Jan. 20, 2010

(86) PCT No.: PCT/JP2010/051004
§ 371 (c)(1),
(2), (4) Date: Sep. 30, 2011

(87) PCT Pub. No.: WO2010/084993
PCT Pub. Date: Jul. 29, 2010

(65) Prior Publication Data
US 2012/0039834 A1    Feb. 16, 2012

(30) Foreign Application Priority Data

Jan. 21, 2009 (JP) ................................. 2009-010515
Jan. 21, 2009 (JP) ................................. 2009-010516

(51) Int. Cl.
*A61K 8/85* (2006.01)
*C08G 64/18* (2006.01)

(52) U.S. Cl.
USPC ............................ 424/70; 525/409; 516/918

(58) Field of Classification Search
None
See application file for complete search history.

(56) References Cited

U.S. PATENT DOCUMENTS

| | | | |
|---|---|---|---|
| 4,533,397 A | | 8/1985 | Wingler et al. |
| 4,866,143 A | * | 9/1989 | Gagnon et al. ............... 525/409 |
| 5,171,830 A | * | 12/1992 | Grey .............................. 528/371 |
| 6,074,628 A | | 6/2000 | Bolich, Jr. et al. |
| 6,113,883 A | | 9/2000 | Midha et al. |
| 2006/0263317 A1 | * | 11/2006 | Adams et al. ............. 424/70.11 |
| 2010/0048935 A1 | | 2/2010 | Mijolovic et al. |
| 2010/0233378 A1 | | 9/2010 | Watanabe et al. |

FOREIGN PATENT DOCUMENTS

| | | |
|---|---|---|
| JP | 2001 507368 | 6/2001 |
| JP | 2008 162945 | 7/2008 |
| WO | 99 47127 | 9/1999 |
| WO | 2008 092767 | 8/2008 |

OTHER PUBLICATIONS

International Search Report issued May 7, 2010 in PCT/JP10/051004 filed Jan. 20, 2010.

Combined Office Action and Search Report issued Aug. 3, 2012 in Chinese Patent Application No. 201080005195.9 with English language translation.

* cited by examiner

*Primary Examiner* — Fereydoun G Sajjadi
*Assistant Examiner* — Yanzhi Zhang
(74) *Attorney, Agent, or Firm* — Oblon, Spivak, McClelland, Maier & Neustadt, L.L.P.

(57) ABSTRACT

A hair cosmetic composition containing a polyether polycarbonate having a structural unit represented by the following formula (1): [wherein A represents a C2 to C6 alkylene group; n represents an average number of 5 to 1,000; p represents an average number of 5 to 100; and (n×p) units of AO may be the same or not].

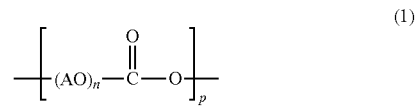

(1)

16 Claims, No Drawings

HAIR COSMETIC COMPOSITION

FIELD OF THE INVENTION

The present invention relates to a hair cosmetic composition containing a specific polymer.

BACKGROUND OF THE INVENTION

For improving hairstyle retention (hereinafter referred to as "hair set retention") provided by a hair cosmetic composition, generally, the amount of a set polymer or oil component incorporated into the hair cosmetic composition is increased. However, when the amount of the set polymer incorporated therein is increased, the styled hair may become hardened or roughened. In general, when hair styling is performed with a hair cosmetic composition containing a set polymer, once the hairstyle is got out of shape after hair styling, the hair cannot be restyled. Meanwhile, when hair styling is performed with a hair cosmetic composition containing an oil component, the hair may be restyled even if the hairstyle is got out of shape. However, hair set retention in the case of using such an oil component is much lower than that of a set polymer. When the oil content of a hair cosmetic composition is increased for improving hair set retention, the hair being styled with the cosmetic composition may become sticky.

In view of the foregoing, there has been proposed a hair cosmetic composition which contains a specific set polymer in order to realize restyling of hair (e.g., Patent Document 1). However, employment of the set polymer which realizes restyling of hair and exhibits sufficient hair set retention may cause stickiness, whereas employment of the set polymer which realizes restyling of hair and causes less stickiness may fail to realize sufficient hair set retention. Thus, producing a hair cosmetic composition which provides sufficient hair set retention and less stickiness, is difficult.

Also, there has been proposed a hair cosmetic composition containing a specific polymer exhibiting "selective self-adhesive property" (i.e., adhering to the same polymer, but hardly adhering to different object), which realizes restyling of hair, exhibits sufficient hair set retention, and causes less stickiness (e.g., Patent Document 2). However, some problems would be caused by using the hair cosmetic composition, i.e., this polymer dissolves only in a specific solvent, so the preparation of the cosmetic composition by dissolving the polymer in a commonly used solvent, such as water or a lower alcohol is restricted, and that, when the adhesive agent adhere to, for example, the user's fingers during handling of the composition, the adhesive agent is difficult to be washed out.

Prior Art Document

Patent Document

Patent Document 1: JP-A-2001-507368

Patent Document 2: JP-A-2008-162945

SUMMARY OF THE INVENTION

The present invention provides a hair cosmetic composition containing a polyether polycarbonate having a structural unit represented by the following formula (1):

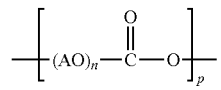

[wherein A represents a C2 to C6 alkylene group; n represents an average number of 5 to 1,000; p represents an average number of 5 to 100; and (n×p) units of AO may be the same or not].

DETAILED DESCRIPTION OF THE INVENTION

The present invention is drawn to a hair cosmetic composition which exhibits sufficient hair set retention, which realizes restyling of hair, and which can employ a commonly used solvent.

The present inventors have found that a polyether polycarbonate having, as a structural unit, a specific polycarbonate structure having an alkyleneoxy chain satisfies the aforementioned requirements, and is suitable as a set polymer employed in a hair cosmetic composition.

[Polyether Polycarbonate]

The polyether polycarbonate employed in the present invention has a structural unit represented by the aforementioned formula (1). In formula (1), A represents a C2 to C6 alkylene group, and (n×p) units of AO may be the same or not. Preferably, the AO units consist of at least two alkyleneoxy groups. In formula (1), A is preferably a C2 to C4 alkylene group, more preferably a C2 or C3 alkylene group. Even more preferably, (n×p) units of AO consist of a combination of an ethyleneoxy group and a propyleneoxy group. When the unit $(AO)_n$ consists of different alkyleneoxy groups, the unit may be a block structure or a random structure. However, more preferably, the unit is a random structure.

In formula (1), n is a number of 5 to 1,000, which corresponds to the average molar amount of added alkyleneoxy groups, and is preferably a number of 10 to 500. In formula (1), p is a number of 5 to 100, which corresponds to the average repetition number of $[(AO)_nCOO]$ groups, and is preferably a number of 5 to 50.

The polyether polycarbonate may be produced through the following method (A) or (B):

(A) a method including a step of transesterification between a carbonate ester and a polyether diol; or (B) a method including a step of reaction between phosgene and a polyether diol.

Even more, the method (A) is preferable.

Examples of the carbonate ester employed in method (A) for producing the polyether polycarbonate include dimethyl carbonate, diphenyl carbonate, diethyl carbonate, ethylene carbonate, and propylene carbonate. Dimethyl carbonate or diphenyl carbonate is preferably employed.

Examples of preferred polyether diols employed for producing the polyether polycarbonate include polyethylene glycol, polypropylene glycol, polytetramethylene glycol, and copolymer of ethylene oxide and propylene oxide. More preferably, a random copolymer produced through copolymerization of ethylene oxide and propylene oxide is employed. The polyether diol employed may be a commercially available one. Examples of the commercially available polyether dial include Adeka Polyethers PR-3005, PR-3007, and PR-5007 (products of Adeka Corporation).

The number average molecular weight of the polyether dial employed in the present invention is preferably 200 to 50,000, more preferably 400 to 20,000, from the viewpoint of good solubility in water or alcohol.

For production of the polyether polycarbonate, an additional polyol may be employed together with any of the aforementioned polyether diols. Examples of the additional polyol include diols such as ethylene glycol, propylene glycol, butanediol, tetramethylene glycol, 2,2-dimethyl-1,3-propanediol, pentanediol, and hexanediol; polyols such as glycerin and pentaerythritol; and aromatic-group-containing diols such as bisphenol A and ethylene oxide adducts of bisphenol A.

When aforementioned glycerin, pentaerythritol, bisphenol A or ethylene oxide adducts of bisphenol A is employed as the additional polyol for transesterification between a carbonate ester and the polyether diol, structural units derived from such an additional polyol are included in the resultant polyether polycarbonate. In this case, similar to the aforementioned case of the unit $(AO)_n$, such a polyol-derived structural unit may have a block structure or a random structure.

The amount of a polyether diol is preferably 50 weight % or more, more preferably 80 weight % or more, even more preferably 90 weight % or more, on the basis of the total amount of polyols.

For transesterification between a carbonate ester and a polyether diol, the molar ratio of the carbonate ester to the polyether diol is preferably from 1/0.9 to 1/1.1, more preferably from 1/0.95 to 1/1.05.

Transesterification between a carbonate ester and a polyether diol may employ a conventional transesterification catalyst. Examples of the transesterification catalyst include alkali metals; alkaline earth metals; and alkoxides, hydrides, hydroxides, carbonate salts, acetate salts and oxides thereof. The transesterification catalyst employed may be an alkoxide, hydride, hydroxide, carbonate salt, acetate salt, or oxide of a metal such as zinc, aluminum, tin, titanium, lead, germanium, antimony, bismuth, nickel, iron, manganese, or zirconium. The transesterification catalyst employed may be an organic base compound such as triethylamine or imidazole. Of these catalysts, alkoxides, hydrides, hydroxides, carbonate salts, acetate salts, and oxides of alkali metals such as sodium, potassium, rubidium, and cesium; alkoxides, hydroxides, carbonate salts, acetate salts, and oxides of metals such as tin and titanium are preferred.

The temperature for transesterification between a carbonate ester and a polyether diol is preferably from 100 to 300° C., more preferably from 120 to 250° C., even more preferably from 120 to 200° C. The reaction may be carried out under ambient pressure, but is preferably carried out under reduced pressure.

In transesterification, preferably, a carbonate ester, a polyether diol and a catalyst are put in and stirred at the aforementioned temperature, and alcohols separated from the carbonate ester is removed outside the reaction system. In the case of being under ambient pressure, the thus-separated alcohols can be effectively removed by passing inert gas (e.g., nitrogen) through the reaction system. In the case of being under reduced pressure, the thus-separated alcohols (i.e., volatile substance) can be readily removed outside the reaction system.

The product produced through the transesterification is preferably subjected to a purification step for removing low-molecular-weight components. By removing the low-molecular-weight components from the product, "other-adhesive force" (adhesion to an object other than the product) can be lowered, leading to realize production of an excellent hair cosmetic composition exhibiting less stickiness.

Removal of low-molecular-weight components can be carried out by, for example, solvent purification. More specifically, the product produced through transesterification is dissolved in a water-soluble solvent, and a hydrophobic solvent is added to the resultant solution in order to thereby precipitate a polyether polycarbonate containing fewer amounts of low-molecular-weight components.

Examples of the water-soluble solvent include alcohol solvents such as methanol, ethanol, and 2-propanol; acetone; and methyl ethyl ketone. Ethanol is preferably employed. Examples of the hydrophobic solvent include hydrocarbon solvents such as hexane and heptane. Hexane is preferably employed. The desired molecular weight distribution of the polyether polycarbonate can be controlled by regulating the ratio of the hydrophobic solvent to the water-soluble solvent. The volume ratio of the hydrophobic solvent to the water-soluble solvent is preferably from 0.1 to 50, more preferably from 0.5 to 10.

The weight average molecular weight of the polyether polycarbonate is preferably 50,000 or more, more preferably 70,000 or more, even more preferably 100,000 or more, even more preferably 150,000 or more, even more preferably 200,000 or more, from the viewpoint of good selective self-adhesive property. The weight average molecular weight of the polyether polycarbonate is preferably 1,000,000 or less, more preferably 700,000 or less, even more preferably 500,000 or less, from the viewpoints of, for example, ease for incorporation thereof into the hair cosmetic composition, as well as ease for washing out from the hair.

As used herein, "the weight average molecular weight of the polyether polycarbonate" or "the number average molecular weight of the polyether diol" is determined by gel permeation chromatography (GPC). More specifically, each of these average molecular weights is determined as polystyrene-equivalent, by means of a GPC system (trade name: HLC-8220GPC, product of Tosoh Corporation) under the following GPC conditions.

<Method for Determining Average Molecular Weight>

Sample concentration: 0.25 weight % (chloroform solution)

Sample injection amount: 100 μL

Eluent: chloroform

Flow rate: 1.0 mL/min

Measurement temperature: 40° C.

Column: "K-G" (trade name, product of Shodex)(×1)+"K-804L" (trade name, product of Shodex)(×2)

Detector: differential refractometer (attached to "HLC-8220GPC" (GPC system), product of Tosoh Corporation)

Polystyrene standard sample: "TSK standard POLYSTYRENE F-10" (molecular weight: 102,000), F-1 (molecular weight: 10,200), and A-1000 (molecular weight: 870) (products of Tosoh Corporation), and "POLYSTYRENE STANDARD" (molecular weight: 900,000, 30,000, product of Nishio Kogyo)

In the case where the selective self-adhesive property of the polyether polycarbonate is represented by physical property values as determined through the method described below (specifically, "self-adhesive force" is defined as physical property value representing adhesion between samples of the same polymer of object), and "other-adhesive force" is defined as physical property value representing adhesion between a sample of a polymer of object and an object that is different from the polymer sample), the ratio of other-adhesive force to self-adhesive force is preferably 0.7 or less, more preferably 0.5 or less, even more preferably 0.3 or less. The polyether polycarbonate preferably has a self-adhesive force of 200 gf or more. More preferably, the self-adhesive force is 200 gf or more and the other-adhesive force is 140 gf or less, more preferably 120 gf or less, even more preferably 100 gf or less.

<Method for Determining Adhesion (Other-Adhesive Force and Self-Adhesive Force)>

A 20 weight % solution of a polymer of object in toluene is prepared and cast the solution as 500 μm thickness onto a PET sheet by means of a bar coater, followed by heating at 60° C. for 12 hours. Thereafter, the resultant product is allowed to stand still at 25° C. and 50% RH for one day. By means of a tacking tester (TAC II UC-2006, product of Rhesca Corporation), the adhesive force between the aforementioned sheet and a material attached to the probe of the tacking tester is determined.

The adhesive force was determined under the following conditions: probe descent speed: 600 mm/sec, probe pressing load: 200 gf, pressing time: 0.5 sec. A polypropylene disk (indenter contact area: 8 mm$^2$, test piece of Engineering Test Service: Noblen NH-8 (product of Mitsubishi Chemical Corporation)) was attached to the tip end of the probe, and the adhesive force between the aforementioned PET sheet and the polypropylene disk was measured. And the measured value is defined as "other-adhesive force". For determination of "self-adhesive force," the polymer of object was dissolved in a solvent in a manner similar to that described above; the solution was cast onto a PET disk (indenter contact area: 8 mm$^2$) and dried; the PET disk was attached to the tip end of the probe; and the adhesive force between the aforementioned PET sheet and the PET disk was measured, and the measured value is defined as "self-adhesive force,".

In the case where the polyether polycarbonate employed in the hair cosmetic composition exhibits the aforementioned selective self-adhesive property, when an adhesive composition which exhibits virtually no or low adhesive force at room temperature, but realizes very high adhesion or re-adhesion between adhesive portions when the portions are attached, is incorporated into a hair-care agent, the resultant hair styling agent realizes both non-stickiness to hands and long-term hair set retention, which have not yet been realized by conventional hair styling materials.

In order to realize higher hair styling performance or hair restyling performance, strong adhesion between hair and the adhesive composition is preferable to be properly maintained. For example, in the case of a hair spray product, when the product is applied to hair, the polymer contained in the product—which is in a plastic form prepared with a solvent—adheres to the hair and wets widely the surface of the hair and enters micro-roughness of the hair, and then fixation (adhesion) of the polymer to the hair is promoted through a drying process (i.e., volatilization of the solvent).

The polyether polycarbonate content of the hair cosmetic composition of the present invention (in the case of aerosol form, it corresponds to the amount in a stock solution; hereinafter the same) is preferably from 0.5 to 20 weight %, more preferably from 1 to 15 weight %, even more preferably from 1.5 to 10 weight %, from the viewpoints of non-stickiness and good hair set retention.

[Anionic polymer]

The hair cosmetic composition of the present invention may also contain an anionic polymer. When the aforementioned polyether polycarbonate is employed in combination with an anionic polymer good selective self-adhesive property over a wider molecular weight range is realized. Examples of the anionic polymer include natural anionic polymers such as xanthan gum, carrageenan, sodium alginate, pectin, furcellaran, gum arabic, gum ghatti, gum karaya, gum tragacanth, agar powder, and carboxymethylcellulose; and synthetic anionic polymers such as polymers produced through polymerization of an acidic vinyl monomer or a salt thereof As used herein, "acidic vinyl monomer" refers to a compound having in the molecule an acidic group (e.g., a carboxy group or a phosphate group) and a polymerizable vinyl group. Examples of the acidic vinyl monomer include acrylic acid, methacrylic acid,crotonic acid, vinylbenzoic acid, itaconic acid, maleic acid, and fumaric acid. Specific examples of the synthetic anionic polymer include carboxylic-acid-containing anionic polymers such as acrylic acid/ethyl acrylate/N-t-butylacrylamide copolymer (e.g., Ultrahold 8 and Ultrahold Strong, products of BASF), octylacrylamide/acrylic acid copolymer (e.g., Amphomer V-42, product of National Starch), acrylate/methacrylate/acrylic acid/methacrylic acid copolymer (e.g., Amerhold DR25, product of Union Carbide Corporation), acrylates/diacetone acrylamide copolymer (e.g., Plus Size L-9540B, product of Goo Chemical Co., Ltd.), methyl vinyl ether/alkyl maleate copolymer (e.g., Gantrez ES-225, Gantrez ES-425, and Gantrez SP-215, products of ISP), vinyl acetate/crotonic acid copolymer (e.g., Resin 28-1310, product of National Starch), vinyl acetate/crotonic acid/vinyl neodecanoate copolymer (e.g., Resin 28-2930, product of National Starch), vinyl acetate/crotonic acid/vinyl propionate copolymer (e.g., Luviset CAP, product of BASF), vinyl alcohol/itaconic acid copolymer (e.g., KM-118, product of Kuraray Co., Ltd.); and phosphate-containing anionic polymers such as homopolymers formed from a phosphate-group-containing monomer (e.g., Polyphosmer M-101, Polyphosmer PE-201, and Polyphosmer MH-301, product of DAP Co., Ltd.), and copolymer of a phosphate-group-containing monomer and an acrylic acid ester (e.g., Polyphosmer MHB-10, product of DAP Co., Ltd.).

The anionic polymer may have a weight average molecular weight of 10,000 to 1,000,000.

Of these anionic polymers, anionic set polymers are preferred, and carboxylic-acid-containing anionic set polymers are more preferred. In particular, unneutralized ones are more preferred.

These anionic polymers may be employed in combination of two or more species. The anionic polymer content of the hair cosmetic composition of the present invention is preferably from 0.5 to 20 weight %, more preferably from 1 to 15 weight %, even more preferably from 1.5 to 10 weight %, from the viewpoints of further reduction of other-adhesive force/self-adhesive force ratio, as well as realization of non-stickiness, good hair set retention, and hair restyling performance.

The ratio by weight of the polyether polycarbonate to the anionic polymer is preferably 20/80 to 80/20, more preferably 30/70 to 70/30, even more preferably 40/60 to 60/40, from the viewpoints of further reduction of other-adhesive force/self-adhesive force ratio, as well as realization of non-stickiness, good hair set retention, and hair restyling performance.

[Other Set Polymer]

For improvement of hair set retention, the hair cosmetic composition of the present invention may contain a set polymer other than the aforementioned anionic hair styling polymers. Examples of such a set polymer include alkylacrylamide/acrylate/alkylaminoalkylacrylamide/poly-ethylene glycol methacrylate copolymer described in JP-A-1990-180911, alkylacrylamide/alkylaminoalkylacrylamide/polyethylene glycol methacrylate copolymer described in JP-A-1996-291206, Yukaformer R205 (product of Mitsubishi Chemical Corporation), (methacryloyloxyethylcarboxybetaine/alkyl methacrylate) copolymer (e.g., RAM Resin, product of Osaka Organic Chemical Industry Ltd.), (acrylates/lauryl acrylate/stearyl acrylate/ethyl methacrylate amine oxide) copolymer (e.g., Diaformer Z-712, product of Mitsubishi Chemical Corporation), (vinylamine/vinyl alcohol) copolymer (e.g., Diafix C-601, product of Mitsubishi Chemical Corporation), polyvinylcaprolactam (e.g., Luviskol Plus, product of BASF), alkyl acrylate copolymer (e.g., Luvimer 100P and Luvimer 30E, products of BASF), (octylacrylamide/hydroxypropyl acrylate/butylaminoethyl methacrylate) copolymer (e.g., Amphomer SH-701, Amphomer 28-4910, Amphomer LV-71, and Amphomer LV-47, products of National Starch & Chemical), (vinylpyrrolidone/dimethylaminoethyl methacrylate) copolymer quaternized with diethyl sulfate (polyquaternium-11) (e.g., Gafquat 440, product of ISP), methyl-quaternized vinylpyrrolidone/dimethylaminopropylmethacrylamide copolymer (polyquaternium-28) (e.g., Gafquat HS-100, product of ISP), (PVP/vinylcaprolactam/DMAPA acrylate) copolymer (e.g., Aquaflex SF-40, product of ISP), (isobutylene/ethylmaleimide/hydroxyethylmaleimide) copolymer (e.g., Aquaflex FX-64, product of ISP), (vinylpyrrolidone/dimethylaminopropylmethacrylamide/meth-acryloylaminopropyllauryldimethylammonium chloride) copolymer (polyquaternium-55) (e.g., Styleze W-20, product of ISP), (vinylpyrrolidone/DMAPA acrylate) copolymer (e.g., Styleze CC-10, product of ISP), and (vinylpyrrolidone/vinyl acetate) copolymer (e.g., PVP/VA735 (product of ISP) and Luviskol VA64P (product of BASF)).

Of the aforementioned set polymers, preferred are alkylacrylamide/acrylate/alkylaminoalkylacrylamide/poly-ethylene glycol methacrylate copolymer, alkylacrylamide/alkylaminoalkylacrylamide/polyethylene glycol methacrylate copolymer, (methacryloyloxyethylcarboxybetaine/alkyl methacrylate) copolymer, (alkyl acrylate/diacetone acrylamide) copolymer neutralized with aminomethyl propanol, (octylacrylamide/hydroxypropyl acrylate/butylaminoethyl methacrylate) copolymer, acrylic acid/acrylamide/ethyl acrylate copolymer, and polyvinylcaprolactam; and more preferred are alkylacrylamide/acrylate/alkylaminoalkylacrylamide/poly-ethylene glycol methacrylate copolymer, and alkylacrylamide/alkylaminoalkylacrylamide/polyethylene glycol methacrylate copolymer.

These set polymers may be employed in combination of two or more species. The set polymer content of the hair cosmetic composition of the present invention is preferably 0.5 to 20 weight %, more preferably 1 to 15 weight %, even more preferably 1.5 to 10 weight %, from the viewpoint of improvement of hair styling performance.
[Medium]

The hair cosmetic composition of the present invention may contain a solvent (supporting medium) such as water, a lower alcohol (e.g., ethanol or isopropanol), or a lactone. These solvents may be employed alone or in combination. Of these solvents, water or ethanol is preferred, in particular, ethanol is more preferred, from the viewpoint of general versatility.
[Optional component]

The hair cosmetic composition of the present invention may contain, in addition to the aforementioned components, an oil component for cosmetic compositions (0.1 to 10 weight %), so long as the oil component does not impede the effects of the present invention. Examples of the oil component include glycerides such as castor oil, cocoa oil, mink oil, avocado oil, and olive oil; waxes such as beeswax, whale wax, lanolin, and carnauba wax; higher alcohols such as cetyl alcohol, oleyl alcohol, lauryl alcohol, stearyl alcohol, isostearyl alcohol, and 2-octyldodecanol; esters such as isopropyl myristate, hexyl laurate, cetyl lactate, propylene glycol monostearate, oleyl oleate, hexadecyl 2-ethylhexanoate, and octyldodecyl myristate; hydrocarbon oils such as liquid paraffin, vaseline, squalane, and hydrogenated polyisobutene; silicone derivatives such as dimethylpolysiloxane, methylphenylpolysiloxane, polyether-modified silicone oil, epoxy-modified silicone oil, amino-modified silicone oil, and alkyl-modified silicone oil; and polypropylene glycol. The hair cosmetic composition may also contain an emulsifier for stabilizing such an oil component through emulsification. The emulsifier employed may be an anionic, amphoteric, cationic, or nonionic surfactant.

The hair cosmetic composition of the present invention may also contain a perfume or a dye for improving its commercial value, or a preservative or an antioxidant for preventing change over time in quality of the hair cosmetic composition. Also, the hair cosmetic composition may optionally contain, for example, a moisture controlling agent (e.g., glycerin or propylene glycol), a curing agent, an antistatic agent, a surfactant, an antifoaming agent, a dispersant, a thickener, a UV-absorbing agent, an antioxidant, a preservative, a coloring dye, a dye fixative, or a propellant.
[Product Form]

Product form of the hair cosmetic composition of the present invention is not particularly limited, and the cosmetic composition may be provided in the form of, for example, transparent liquid, lotion, emulsion, spray (aerosol), or mousse (aerosol foam).

An aerosol hair cosmetic product is produced by filling the hair cosmetic composition of the present invention into a pressure-resistant container together with a propellant. Examples of the propellant include liquefied petroleum gas (LPG), dimethyl ether (DME), carbon dioxide gas, nitrogen gas, and a mixture thereof. The propellant employed may be hydrofluorocarbon (e.g., HFC-152a). In such an aerosol hair cosmetic product, the ratio by weight of a stock solution to a propellant is preferably 5/95 to 99/1, more preferably 20/80 to 95/5, from the viewpoint of good spray performance and good adhesion. Preferably, the pressure in the pressure-resistant container is regulated to 0.12 to 0.45 MPa at 25° C., so as to realize good spray performance and good adhesion.

EXAMPLES

In the Examples described below, the weight average molecular weight and adhesion (other-adhesive force and self-adhesive force) of a polyether polycarbonate were determined through the aforementioned methods.

For determination of the weight average molecular weight of comparative polymer 1, the measurement was performed through the aforementioned conditions, except that the column was replaced with "TSK guard column HHR-H" (trade name, product of Tosoh corporation)(×1)+"TSK gel GMHHR-H" (trade name, product of Tosoh corporation)(× 2).

Synthetic Example 1

A random copolymer of ethylene oxide and propylene oxide (number average molecular weight: 5,000, hydroxyl value: 22.0 mg-KOH/g, product of Adeka Corporation, trade name: Adeka Polyether PR-5007) (500.9 g, 0.099 mol), diphenyl carbonate (21.25 g, 0.099 mol), and tert-butoxypotassium (22 mg, 0.2 mmol) were added to a reaction vessel equipped with a stirrer, a fractionating condenser, and a thermometer.

The mixture contained in the reaction vessel was heated to 120° C. while stirring, and then reduced-pressure suction was started by means of a vacuum pump. The temperature was further elevated to 150° C., and phenol produced through reaction was discharged outside the reaction system. Thereafter, heating was continued for three hours, to thereby yield a polyether polycarbonate (hereinafter may be referred to as "polyether polycarbonate 1"). Polyether polycarbonate 1 was found to have a weight average molecular weight of 50,000.

The resulted polyether polycarbonate 1 exhibited excellent selective self-adhesive property.

Synthetic Example 2

A random copolymer of ethylene oxide and propylene oxide (number average molecular weight: 5,000, hydroxyl value: 22.0 mg-KOH/g, product of Adeka Corporation, trade name: Adeka Polyether PR-5007) (500.2 g, 0.099 mol), diphenyl carbonate (21.22 g, 0.099 mol), and potassium carbonate (51 mg, 0.4 mmol) were added to a reaction vessel equipped with a stirrer, a fractionating condenser, and a thermometer.

The mixture contained in the reaction vessel was heated to 120° C. while stirring, and then reduced-pressure suction was started by means of a vacuum pump. The temperature was further elevated to 150° C., and phenol produced through reaction was discharged outside the reaction system. Thereafter, heating was continued for 26 hours, to thereby yield a polyether polycarbonate (hereinafter may be referred to as "polyether polycarbonate 2"). Polyether polycarbonate 2 was found to have a weight average molecular weight of 130,000.

Polyether polycarbonate 2 exhibited excellent selective self-adhesive property.

Synthetic Example 3

A random copolymer of ethylene oxide and propylene oxide (number average molecular weight: 5,000, hydroxyl value: 22.0 mg-KOH/g, product of Adeka Corporation, trade name: Adeka Polyether PR-5007) (27.1 g, 0.005 mol), diphenyl carbonate (1.15 g, 0.005 mol), and cesium carbonate (4 mg, 0.01 mmol) were added to a reaction vessel equipped with a stirrer, a fractionating condenser, and a thermometer.

The mixture contained in the reaction vessel was heated to 160° C. while stirring; heating was continued for two hours; and phenol produced through reaction was discharged outside the reaction system. Subsequently, reduced-pressure suction was started by means of a vacuum pump, and, while the temperature was gradually elevated to 180° C., reaction was continued for about four hours, to thereby yield a polyether polycarbonate (hereinafter may be referred to as "polyether polycarbonate 3"). Polyether polycarbonate 3 was found to have a weight average molecular weight of 180,000.

Polyether polycarbonate 3 was found to have an other-adhesive force of 106 gf and a self-adhesive force of 233 gf; i.e., other-adhesive force/self-adhesive force was 0.45.

Synthetic Example 4

Polyether polycarbonate 3 produced in Synthetic Example 3 (10 g) was dissolved in ethanol (100 mL), and a double volume of hexane was added thereto and mixed with shaking, followed by recovery of the resultant precipitate. The thus-recovered polymer (hereinafter referred to as "polyether polycarbonate 4") was found to have a weight average molecular weight of 257,000.

An other-adhesive force was 25 gf, and a self-adhesive force was 381 gf; other-adhesive force/self-adhesive force was 0.07.

Synthetic Example 5

A random copolymer of ethylene oxide and propylene oxide (number average molecular weight: 5,000, hydroxyl value: 22.0 mg-KOH/g, product of Adeka Corporation, trade name: Adeka Polyether PR-5007) (99 g, 0.02 mol), diphenyl carbonate (4.2 g, 0.02 mol), and potassium carbonate (16 mg, 0.1 mmol) were added to a reaction vessel equipped with a stirrer, a fractionating condenser, and a thermometer.

The mixture contained in the reaction vessel was heated to 120° C. while stirring, and then reduced-pressure suction was started by means of a vacuum pump. The temperature was further elevated to 145° C., and phenol produced through reaction was discharged outside the reaction system. Thereafter, heating was continued for 4.5 hours, to thereby yield a polyether polycarbonate (hereinafter may be referred to as "polyether polycarbonate 5"). Polyether polycarbonate 5 was found to have a weight average molecular weight of 210,000.

An other-adhesive force was 70 gf and a self-adhesive force was 324 gf, other-adhesive force/self-adhesive force was 0.22.

Synthetic Example 6

A random copolymer of ethylene oxide and propylene oxide (number average molecular weight: 5,000, hydroxyl value: 22.0 mg-KOH/g, product of Adeka Corporation, trade name: Adeka Polyether PR-5007) (560.1 g, 0.11 mol), diphenyl carbonate (23.77 g, 0.11 mol), and a 1M solution of tert-butoxypotassium in tert-butanol (product of Aldrich) (0.10 mL, 0.1 mmol as reduced to tert-butoxypotassium) were added to a reaction vessel equipped with a stirrer, a fractionating condenser, and a thermometer.

The mixture contained in the reaction vessel was heated to 120° C. while stirring, and then reduced-pressure suction was started by means of a vacuum pump. The temperature was further elevated to 160° C., and phenol produced through reaction was discharged outside the reaction system. Thereafter, heating was continued for three hours, to thereby yield a polyether polycarbonate (hereinafter may be referred to as "polyether polycarbonate 6"). Polyether polycarbonate 6 was found to have a weight average molecular weight of 20,000.

Polyether polycarbonate 6 exhibited excellent selective self-adhesive property.

Each of polyether polycarbonates 1 to 6 produced in Synthetic Examples 1 to 6 (7.5 g each) was added to a hermetically sealable glass container (transparent wide-mouth glass bottle No. 13, mouth inner diameter: 31.9 mm×bottle diameter: 58.0 mm×height: 115.0 mm), and ethanol was added thereto up to 100 g, followed by stirring at room temperature (25° C.) for 24 hours by means of a magnetic stirrer (length: 30 mm×diameter: 8 mm) (800 r/m). Thereafter, the container was allowed to stand still for 24 hours, and solubility of the polymer in ethanol was evaluated on the basis of the presence or absence of solid substance in the ethanol solution. As a result, all of polyether polycarbonates 1 to 6 were found to dissolve in ethanol.

Synthetic Example 7

A 1/10 amount of a mixture of acrylic acid (67 g), stearyl acrylate (33 g), and isopropyl alcohol (solvent for polymerization) (67 g) was added to a reactor equipped with a dropping funnel, a stirrer, a reflux condenser, a thermometer, and a nitrogen-introduction tube, and the remainder of the mixture and a polymerization initiator (V-65, product of Wako Pure Chemical Industries, Ltd.) (0.5 g) were added dropwise with the dropping funnel at 75° C. over 2.5 hours. After completion of dropwise addition, followed by aging for one hour, then the initiator V-65 (0.2 g) was added every 30 minutes for thrice. Thereafter, the reaction temperature was elevated to 80° C., and reaction was completed after one hour had passed. Unreacted monomer and the residual initiator were removed from the reaction product by means of a purifier with an alumina ceramic membrane having a pore size of 500 Å, followed by drying, to thereby yield an anionic amphiphilic polymer (hereinafter referred to as "anionic polymer 3"). Anionic polymer 3 was found to have a weight average molecular weight of 35,000. Anionic polymer 3 was found to have an acrylic acid structural unit content of 67 weight %, and a stearyl acrylate structural unit content of 33 weight %.

Comparative Synthetic Example 1

Polycarbonate diol (PLACCEL CD220PL, number average molecular weight: 2,000, hydroxyl value: 58.4 mg-KOH/g, product of Daicel Chemical Industries, Ltd.) (51.4 g, 0.027 mol), sebacic acid (5.4 g, 0.027 mol), p-toluenesulfonic acid (0.2 g, 0.001 mol), and toluene (120 mL) were added to a reaction vessel equipped with a stirrer, a reflux condenser (via water-separating tube), and a thermometer.

The mixture contained in the reaction vessel was heated to 150° C. while stirring; heating was continued for five hours; and water produced through reaction was discharged outside the reaction system together with toluene, to yield comparative polymer 1.

The weight average molecular weight of comparative polymer 1 was determined through gel permeation chromatography (GPC) using polystyrene gel. Comparative polymer 1 was found to have a weight average molecular weight of 50,700 (the molecular weight was calibrated with a polystyrene standard sample).

An other-adhesive force was 50 gf and a self-adhesive force was 350 gf, other-adhesive force/self-adhesive force was 0.14.

In a manner similar to that described above, solubility of comparative polymer 1 produced in Comparative Synthetic Example 1 in ethanol was evaluated. As a result, comparative polymer 1 was found not to dissolve in ethanol.

Examples 1 to 24 and Comparative Examples 1 to 4

Pump mists, according to formulations shown in Tables 1 to 3, were prepared using the polymers produced in the Synthetic Examples and the Comparative Synthetic Example. These pump mists were evaluated through the evaluation methods described below.
[Evaluation Methods]
Evaluation of Stickiness to Fingers
A hair tress (length: 10 cm, width: 2 cm) was wetted with water and then dried with a towel. Thereafter, the hair tress was wound around a rod having a diameter of 4 cm, and then allowed to stand still at 25° C. and 65% RH for 24 hours. Each of the hair cosmetic compositions prepared according to the formulations (2 g) was applied to the hair tress by means of a pump mist container, and the hair tress was allowed to stand still at 25° C. and 65% RH for two hours for drying. Thereafter, the rod was removed from the hair tress, to thereby prepare an evaluation sample. Feel to the touch of the evaluation sample was evaluated by an expert panelist according to the following criteria:
A: no stickiness;
B: virtually no stickiness;
C: slight stickiness; and
D: stickiness.
Evaluation of Roughness
An evaluation sample was prepared in a manner similar to that described above, and feel to the touch of the evaluation sample was evaluated by an expert panelist according to the following criteria:
A: no roughness;
B: virtually no roughness;
C: slight roughness; and
D: roughness.
Evaluation of Styling Performance
An evaluation sample was prepared in a manner similar to that described above, and styling performance of the sample was evaluated by an expert panelist according to the following criteria:
A: high hair styling performance;
B: slightly high hair styling performance;
C: slightly low hair styling performance; and
D: low or no hair styling performance.
Evaluation of Restyling Performance
An evaluation sample, prepared in a manner similar to that described above, was combed five times with Delrin Smooth Comb #802 (straight) (Takigawa Co., Ltd). Thereafter, the sample was again wound around a rod having a diameter of 4 cm, and then allowed to stand still at 25° C. and 65% RH for one hour for hair restyling. Restyling performance of the sample was evaluated by an expert panelist according to the following criteria:
A: high hair restyling performance;
B: slightly high hair restyling performance;
C: slightly low hair restyling performance; and
D: low or no hair restyling performance.
Evaluation of Hair Set Retention
An evaluation sample, prepared in a manner similar to that described above, was suspended at 25° C. and 65% RH for eight hours. Hair set retention of the sample was evaluated by an expert panelist according to the following criteria:
A: high hair set retention;
B: slightly high hair set retention;
C: slightly low hair set retention; and
D: low or no hair set retention.

TABLE 1

| (weight %) | Examples | | | Comparative Examples | | |
|---|---|---|---|---|---|---|
| | 1 | 2 | 3 | 1 | 2 | 3 |
| Polyether polycarbonate 3 (Mw 180,000) | 7.5 | — | — | — | — | — |
| Polyether polycarbonate 4 (Mw 257,000) | — | 7.5 | — | — | — | — |
| Polyether polycarbonate 5 (Mw 210,000) | — | — | 7.5 | — | — | — |
| Comparative polymer 1 (Mw 50,700) | — | — | — | — | — | 7.5 |

TABLE 1-continued

|  | (weight %) | Examples 1 | Examples 2 | Examples 3 | Comparative Examples 1 | Comparative Examples 2 | Comparative Examples 3 |
|---|---|---|---|---|---|---|---|
|  | Set polymer (Plus Size L-9540B, Goo Chemical Co., Ltd.) | — | — | — | 3.0 | 7.5 | — |
|  | Isostearyl glyceryl ether | — | — | — | 4.5 | — | — |
|  | Ethanol | Balance | Balance | Balance | Balance | Balance | Balance |
| Evaluation | Non-Stickiness | B | B | B | D | B | — |
|  | Non-Roughness | A | A | A | B | D | — |
|  | Styling performance | B | A | A | A | A | — |
|  | Restyling performance | B | A | B | A | D | — |

TABLE 2

|  | (weight %) | Examples 4 | 5 | 6 | 7 | 8 | 9 | 10 | 11 | 12 | 13 | 14 |
|---|---|---|---|---|---|---|---|---|---|---|---|---|
| (A) | Polyether polycarbonate 1 (Mw 50,000) | — | — | — | — | — | — | — | — | — | — | — |
|  | Polyether polycarbonate 2 (Mw 130,000) | — | — | — | — | — | — | — | — | — | — | — |
|  | Polyether polycarbonate 3 (Mw 180,000) | 3.75 | 3.75 | 3.75 | 1.50 | 3.00 | 4.50 | 6.00 | 1.50 | 3.00 | 4.50 | 6.00 |
|  | Polyether polycarbonate 4 (Mw 257,000) | — | — | — | — | — | — | — | — | — | — | — |
|  | Polyether polycarbonate 6 (Mw 20,000) | — | — | — | — | — | — | — | — | — | — | — |
| (B) | Anionic polymer 1 (Gantrez ES-425, ISP) | 3.75 | — | 1.88 | 6.00 | 4.50 | 3.00 | 1.50 | — | — | — | — |
|  | Anionic polymer 2 (Plus Size L-9540B, Goo Chemical Co., Ltd.) | — | 3.75 | 1.88 | — | — | — | — | 6.00 | 4.50 | 3.00 | 1.50 |
|  | Anionic polymer 3 (alkyl (C18) acrylate/acrylic acid (33/67) copolymer; Mw 35,000) | — | — | — | — | — | — | — | — | — | — | — |
|  | Anionic polymer 4 (Polyphosmer M-101, DAP Co., Ltd.) | — | — | — | — | — | — | — | — | — | — | — |
|  | Ethanol | Balance | Balance | Balance | Balance | Balance | Balance | Balance | Balance | Balance | Balance | Balance |
| Evaluation | Non-Stickiness | B | B | A | A | B | B | B | B | B | B | B |
|  | Non-Roughness | A | A | A | B | A | A | B | A | A | A | A |
|  | Styling performance | A | A | A | B | B | A | B | A | B | A | B |
|  | Restyling performance | A | A | A | B | B | B | B | B | B | B | B |
|  | Hair set retention | B | B | A | B | B | B | B | B | B | B | B |

TABLE 3

|  | (weight %) | Examples 15 | 16 | 17 | 18 | 19 | 20 | 21 | 22 | 23 | 24 | Comparative Example 4 |
|---|---|---|---|---|---|---|---|---|---|---|---|---|
| (A) | Polyether polycarbonate 1 (Mw 50,000) | 3.75 | — | — | — | — | — | — | — | — | — | — |
|  | Polyether polycarbonate 2 (Mw 130,000) | — | 3.75 | — | — | — | — | — | — | — | — | — |
|  | Polyether polycarbonate 3 (Mw 180,000) | — | — | — | 3.75 | 3.75 | 3.75 | 3.75 | — | 6.75 | 0.75 | — |
|  | Polyether polycarbonate 4 (Mw 257,000) | — | — | 3.75 | — | — | — | — | — | — | — | — |
|  | Polyether polycarbonate 6 (Mw 20,000) | — | — | — | — | — | — | — | 3.50 | — | — | — |
| (B) | Anionic polymer 1 (Gantrez ES-425, ISP) | 3.75 | 3.75 | 3.75 | 1.00 | 2.75 | — | — | 3.50 | — | — | 7.50 |
|  | Anionic polymer 2 (Plus Size L-9540B, Goo Chemical Co., Ltd.) | — | — | — | 2.75 | 1.00 | — | — | — | — | — | — |
|  | Anionic polymer 3 (alkyl (C18) acrylate/acrylic acid (33/67) copolymer; Mw 35,000) | — | — | — | — | — | 3.75 | — | — | 0.75 | 6.75 | — |
|  | Anionic polymer 4 (Polyphosmer M-101, DAP Co., Ltd.) | — | — | — | — | — | — | 3.75 | — | — | — | — |
|  | Ethanol | Balance | Balance | Balance | Balance | Balance | Balance | Balance | Balance | Balance | Balance | Balance |
| Evaluation | Non-Stickiness | B | B | B | A | A | B | A | A | B | A | A |
|  | Non-Roughness | A | A | A | A | A | B | B | B | B | C | D |
|  | Styling performance | B | A | A | A | A | A | A | B | B | B | A |
|  | Restyling performance | B | A | A | A | A | B | A | C | B | C | D |
|  | Hair set retention | B | B | A | A | A | B | A | C | C | B | B |

Example 25

A hair cream having the following composition was produced through a usual method.

| | |
|---|---|
| Polyether polycarbonate 5 | 1.0 (weight %) |
| Polyoxyethylene (E.O.6) stearyl ether | 1.5 |
| Beeswax | 1.0 |
| Perfume | Appropriate amount |
| Preservative | Appropriate amount |
| Water | Balance |
| Total | 100.0 |

Example 26

A hair liquid having the following composition was produced through a usual method.

| | |
|---|---|
| Polyether polycarbonate 4 | 1.0 (weight %) |
| Propylene glycol | 2.0 |
| Ethanol | 45.0 |
| Perfume | Appropriate amount |
| Colorant | Appropriate amount |
| Water | Balance |
| Total | 100.0 |

Example 27

A hair conditioner having the following composition was produced through a usual method.

| | |
|---|---|
| Polyether polycarbonate 4 | 1.0 (weight %) |
| Cetyltrimethylammonium chloride | 0.75 |
| Cetostearyl alcohol | 1.0 |
| Glyceryl monostearate | 0.5 |
| Perfume | Appropriate amount |
| Water | Balance |
| Total | 100.0 |

Example 28

A hair styling foam (mousse) having the following composition was produced through a usual method.

| | |
|---|---|
| Hair conditioner of Example 27 | 90 (weight %) |
| Propellant (LPG: 60 weight %, DME: 40 weight %) | 10 |
| Total | 100 |

Example 29

A hair liquid having the following composition was produced through a usual method.

| | |
|---|---|
| Polyether polycarbonate 3 | 2.5 (weight %) |
| Propylene glycol | 3.0 |
| Ethanol | 40.0 |
| Perfume | Appropriate amount |
| Water | Balance |
| Total | 100.0 |

Example 30

A hair styling mist (spray) was produced by charging, into a pressure-resistant container, a stock solution having the following composition and a propellant (LPG: 60%, DME: 40%) so that the ratio of the stock solution/the propellant was 50/50.

| | |
|---|---|
| Polyether polycarbonate 5 | 7.5 (weight %) |
| Perfume | Appropriate amount |
| Ethanol | Balance |
| Total | 100.0 |

Example 31

A hair styling mist (spray) was produced by charging, into a pressure-resistant container, a stock solution having the following composition and a propellant (LPG: 60%, DME: 40%) so that the ratio of the stock solution/the propellant was 50/50.

| | |
|---|---|
| Polyether polycarbonate 3 | 2.0 (weight %) |
| Perfume | Appropriate amount |
| Ethanol | Balance |
| Total | 100.0 |

Example 32

A hair gel having the following composition was produced through a usual method.

| | |
|---|---|
| Polyether polycarbonate 5 | 2.0 (weight %) |
| Carboxyvinyl polymer (*1) | 1.0 |
| Concentrated glycerin | 5.0 |
| Triethanolamine solution (89 weight %) | 1.3 |
| Ethanol | 10.0 |
| Perfume | Appropriate amount |
| Water | Balance |
| Total | 100.0 |

(*1): Carbopol 940

Example 33

A hair wax having the following composition was produced through a usual method.

| | |
|---|---|
| Polyether polycarbonate 5 | 10.0 (weight %) |
| Anionic polymer 1 | 5.0 |
| Glycerin | 5.0 |
| Carbomer (*2) | 0.1 |
| Cetanol | 5.0 |
| Glyceryl stearate | 5.0 |
| Polysorbate 60 | 1.0 |
| Microcrystalline wax | 0.5 |
| Beeswax | 0.5 |
| Vaseline | 0.5 |
| Dimethicone | 2.0 |
| Octyldodecyl myristate | 0.5 |
| Ethanol | 5.0 |
| Perfume | 0.05 |
| pH adjusting agent (sodium hydroxide) | Adjusted to pH 6.5 |
| Water | Balance |
| Total | 100.0 |

(*2): Product of Lubrizol Corporation, Carbopol 981

Example 34

A hair cream having the following composition was produced through a usual method.

| | |
|---|---|
| Polyether polycarbonate 3 | 1.0 (weight %) |
| Anionic polymer 1 | 1.0 |
| Polyoxyethylene (E.O.6) stearyl ether | 1.5 |
| Beeswax | 1.0 |
| Perfume | Appropriate amount |
| Preservative | Appropriate amount |
| Water | Balance |
| Total | 100.0 |

Example 35

A hair liquid having the following composition was produced through a usual method.

| | |
|---|---|
| Polyether polycarbonate 2 | 1.5 (weight %) |
| Anionic polymer 2 | 1.5 |
| Propylene glycol | 2.0 |
| Ethanol | 45.0 |
| Perfume | Appropriate amount |
| Colorant | Appropriate amount |
| Water | Balance |
| Total | 100.0 |

Example 36

A hair conditioner having the following composition was produced through a usual method.

| | |
|---|---|
| Polyether polycarbonate 2 | 2.0 (weight %) |
| Anionic polymer 2 | 2.0 |
| Cetyltrimethylammonium chloride | 0.75 |
| Cetostearyl alcohol | 1.0 |
| Glyceryl monostearate | 0.5 |
| Perfume | Appropriate amount |
| Water | Balance |
| Total | 100.0 |

Example 37

A hair styling foam (mousse) having the following composition was produced through a usual method.

| | |
|---|---|
| Hair conditioner of Example 36 | 90 (weight %) |
| Propellant (LPG: 60 weight %, DME: 40 weight %) | 10 |
| Total | 100 |

Example 38

A hair liquid having the following composition was produced through a usual method.

| | |
|---|---|
| Polyether polycarbonate 3 | 2.5 (weight %) |
| Anionic polymer 1 | 2.5 |
| Propylene glycol | 3.0 |
| Ethanol | 40.0 |
| Perfume | Appropriate amount |
| Water | Balance |
| Total | 100.0 |

Example 39

A hair styling mist (spray) was produced by charging, into a pressure-resistant container, a stock solution having the following composition and a propellant (LPG: 40%, DME: 60%) so that the ratio of the stock solution/the propellant was 50/50.

| | |
|---|---|
| Polyether polycarbonate 3 | 3.75 (weight %) |
| Anionic polymer 1 | 3.75 |
| Perfume | Appropriate amount |
| Ethanol | Balance |
| Total | 100.0 |

Example 40

A hair styling mist (spray) was produced by charging, into a pressure-resistant container, a stock solution having the following composition and a propellant (LPG: 60%, DME: 40%) so that the ratio of the stock solution/the propellant was 50/50.

| | |
|---|---|
| Polyether polycarbonate 3 | 3.75 (weight %) |
| Anionic polymer 2 | 3.75 |
| Perfume | Appropriate amount |
| Ethanol | Balance |
| Total | 100.0 |

Example 41

A hair styling mist (spray) was produced by charging, into a pressure-resistant container, a stock solution having the following composition and a propellant (LPG: 40%, DME: 60%) so that the ratio of the stock solution/the propellant was 50/50.

| | |
|---|---|
| Polyether polycarbonate 3 | 3.75 (weight %) |
| Anionic polymer 1 | 1.88 |
| Perfume | Appropriate amount |
| Ethanol | Balance |
| Total | 100.0 |

Example 42

A hair gel having the following composition was produced through a usual method.

| | |
|---|---|
| Polyether polycarbonate 3 | 5.0 (weight %) |
| Anionic polymer 1 | 5.0 |
| Carboxyvinyl polymer (*1) | 1.0 |
| Concentrated glycerin | 5.0 |
| Triethanolamine solution (89 weight %) | 1.3 |
| Ethanol | 10.0 |
| Perfume | Appropriate amount |
| Water | Balance |
| Total | 100.0 |

(*1): Carbopol 940

Example 43

A hair wax having the following composition was produced through a usual method.

| | |
|---|---|
| Polyether polycarbonate 3 | 5.0 (weight %) |
| Anionic polymer 1 | 5.0 |
| Glycerin | 5.0 |
| Carbomer (*2) | 0.1 |
| Cetanol | 5.0 |
| Glyceryl stearate | 5.0 |
| Polysorbate 60 | 1.0 |
| Microcrystalline wax | 0.5 |
| Beeswax | 0.5 |
| Vaseline | 0.5 |
| Dimethicone | 2.0 |
| Octyldodecyl myristate | 0.5 |
| Ethanol | 5.0 |
| Perfume | 0.05 |
| pH adjusting agent (sodium hydroxide) | Adjusted to pH 6.5 |
| Water | Balance |
| Total | 100.0 |

(*2): Product of Lubrizol Corporation, Carbopol 981

The hair cosmetic composition produced in each of the aforementioned Examples exhibited excellent selective self-adhesive property. When a usual amount of the composition was applied to hair, the composition exhibited excellent hair styling performance and hair restyling performance, but did not provide an unpleasant feel to the touch (e.g., roughness of the hair or stickiness to hands) during hair styling.

The invention claimed is:

1. A hair setting method, comprising contacting hair of a subject in need thereof with a composition comprising a polyether polycarbonate having a structural unit of formula (1):

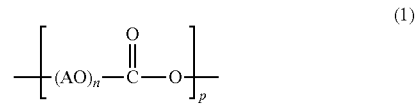

wherein A represents a C2 to C6 alkylene group; n represents a number of 5 to 1,000; p represents a number of 5 to 100; and (n×p) units of AO may be the same or not.

2. The method according to claim 1, wherein the polyether polycarbonate has a weight average molecular weight of 50,000 to 1,000,000.

3. The method according to claim 1, wherein (n×p) units of AO in formula (1) consist of at least two alkyleneoxy groups.

4. The method according to claim 3, wherein (n×p) units of AO in formula (1) consist of a combination of an ethyleneoxy group and a propyleneoxy group.

5. The method according to claim 3, wherein the unit $(AO)_n$ in formula (1) has a random structure.

6. The method according to claim 1, wherein the polyether polycarbonate is a product by a production method including a step of transesterification between a carbonate ester and a polyether diol.

7. The method according to claim 6, wherein the polyether polycarbonate is a product produced by using a polyether diol having a number average molecular weight of 200 to 50,000.

8. The method according to claim 6, wherein the polyether polycarbonate is a product produced through a purification step for removing low-molecular weight components from a product produced by transesterification.

9. The method according to claim 1, wherein the composition further comprises an anionic polymer.

10. The method according to claim 9, wherein the anionic polymer has a weight average molecular weight of 10,000 to 1,000,000.

11. The method according to claim 9, wherein the anionic polymer has unneutralized acidic groups.

12. The method according to claim 9, wherein the ratio by weight of the polyether polycarbonate to the anionic polymer is from 20/80 to 80/20.

13. The method according to claim 1, wherein n is 10 to 500.

14. The method according to claim 1, wherein p is 5 to 50.

15. The method according to claim 13, wherein p is 5 to 50.

16. The method according to claim 1, wherein the polyether polycarbonate has a weight average molecular weight of 200,000 to 500,000.

* * * * *